(12) United States Patent
Wagner et al.

(10) Patent No.: US 10,918,344 B2
(45) Date of Patent: Feb. 16, 2021

(54) METHODS AND SYSTEMS FOR DETERMINING VASCULAR VELOCITY USING CT IMAGING

(71) Applicant: WISCONSIN ALUMNI RESEARCH FOUNDATION, Madison, WI (US)

(72) Inventors: Martin G. Wagner, Madison, WI (US); Charles A. Mistretta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 37 days.

(21) Appl. No.: 16/424,436

(22) Filed: May 28, 2019

(65) Prior Publication Data

US 2019/0365336 A1 Dec. 5, 2019

Related U.S. Application Data

(60) Provisional application No. 62/677,543, filed on May 29, 2018.

(51) Int. Cl.
*A61B 6/03* (2006.01)
*A61B 6/00* (2006.01)
*A61B 5/026* (2006.01)
*A61B 5/02* (2006.01)
*A61B 5/00* (2006.01)

(52) U.S. Cl.
CPC .............. *A61B 6/032* (2013.01); *A61B 6/481* (2013.01); *A61B 6/504* (2013.01); *A61B 5/0073* (2013.01); *A61B 5/026* (2013.01); *A61B 5/02007* (2013.01); *A61B 6/507* (2013.01); *A61B 6/5205* (2013.01)

(58) Field of Classification Search
CPC ....... A61B 5/026; A61B 5/0073; A61B 6/032; A61B 6/504
See application file for complete search history.

(56) References Cited

U.S. PATENT DOCUMENTS

| 6,073,042 A * | 6/2000 | Simonetti ............ A61B 5/055 324/307 |
| 2017/0003369 A1* | 1/2017 | Hwang ............ G01R 33/56366 |
| 2018/0184911 A1* | 7/2018 | Lavi ...................... A61B 6/507 |
| 2018/0256042 A1* | 9/2018 | Beckers ................ A61B 5/026 |

* cited by examiner

*Primary Examiner* — John J Lee
(74) *Attorney, Agent, or Firm* — Foley & Lardner LLP

(57) ABSTRACT

Systems and methods for estimating arterial flow information can include a processor generating a time attenuation sequence for each point of a pair of points along a segment of a coronary artery structure. The processor can determine the arterial flow velocity between the pair of points using the distance between the pair of points and the difference between average transit times associated with the pair of points. The one or more processors can determine the average transit times across the same time window. The processor can determine the arterial flow velocity between the pair of points using the distance between the pair of points and the difference between a first time duration that a number of particles take to pass by a first point of the pair of points and a second time duration that the number of particles take to pass by the other point.

20 Claims, 9 Drawing Sheets

METHODS AND SYSTEMS FOR DETERMINING VASCULAR VELOCITY USING CT IMAGING

CROSS-REFERENCE TO RELATED APPLICATION

This application claims priority to, and the benefit of, U.S. provisional application No. 62/677,543 filed on May 29, 2018, and titled "METHODS AND SYSTEMS FOR DETERMINING VASCULAR VELOCITY USING CT IMAGING," which is incorporated by reference herein in its entirety.

BACKGROUND OF THE DISCLOSURE

Computed tomography (CT) allows for imaging interior anatomical regions and organs in patients and provides valuable diagnosis information. For instance, CT projection images can provide visual depictions of the structures of internal organs, blood vessels, tissues, or a combination thereof. Such visual depictions can allow, for example, for the detection and localization of abnormalities, such as tumors, bone fractures, abscesses, abnormal blood vessels, or blood clots.

CT angiography (CTA) is a CT imaging modality that produces detailed CT projection images of both blood vessels and tissues in an anatomical body (e.g., a patient or animal). A contrast agent (e.g., an iodine-rich dye) can be injected in a vein of the anatomical body to increase the contrast of blood vessels, for example, compared to soft tissues. A CT scanner can acquire a plurality of CT projection images while, or after, the contrast agent moves into the vessels within an anatomical region of interest. The acquisition of a sequence of CT projection images can allow for tracking of the movement of the contrast agent into blood vessels within the imaged anatomical region.

SUMMARY OF THE DISCLOSURE

According to at least one aspect, a method of generating arterial flow signals based on computed tomography projections can include obtaining a three-dimensional (3D) image of an anatomical region including a coronary artery structure. The method can include constructing a 3D centerline of the coronary artery structure by removing voxels of the coronary artery structure in the 3D image to reduce a thickness of the coronary artery structure. The constructing of the 3D centerline can include determining, at voxels along the 3D centerline, one or more corresponding diameters of the coronary artery structure. The method can include projecting the 3D centerline on each CT projection image of a set of CT projection images to identify one or more respective two-dimensional (2D) centerlines of the coronary artery structure on the CT projection image. The method can include determining, for each pixel of the one or more 2D centerlines of the coronary artery structure, a corresponding background intensity value using a diameter of the coronary artery structure associated with the pixel of the one or more 2D centerlines of the coronary artery structure. The method can include subtracting, from each pixel of the one or more 2D centerlines of the coronary artery structure, the corresponding background intensity value to generate arterial pixel intensity values along the one or more 2D centerlines of the coronary artery structure with mitigated background interference.

According to at least one other aspect, a method of estimating arterial flow velocity in coronary arteries based on computed tomography (CT) projections can include obtaining a sequence of computed tomography (CT) projection images of an anatomical region including a coronary artery structure. The sequence of CT projection images can be acquired by a CT scanner at a plurality of acquisition time instances. The method can include generating, for a first point along a segment of the coronary artery structure, a corresponding first time attenuation sequence representing intensity values of the first point across the sequence of the CT projection images. The method can include generating, for a second point along the segment of the coronary artery structure and different than the first point, a corresponding second time attenuation sequence representing intensity values of the second point across the sequence of the CT projection images. The method can include determining, using the first time attenuation sequence and a time window, a first average transit time value representing an average time duration for arterial flow particles to reach the first point along the segment of the coronary artery structure. The method can include determining, using the second time attenuation sequence and the time window, a second average time value representing an average time duration for arterial flow particles to reach the second point along the segment of the coronary artery structure. The method can include determining an arterial flow velocity value between the first and second points along the segment of the coronary artery structure as a distance between the first and second points along the segment of the coronary artery structure divided by an absolute difference between the first and second average transit time values.

According to at least one other aspect, a method of estimating arterial flow velocity in coronary arteries based on computed tomography (CT) projections can include obtaining a sequence of computed tomography (CT) projection images of an anatomical region including a coronary artery structure. The method can include generating, for a first point along a segment of the coronary artery structure, a corresponding first time attenuation sequence representing the intensity of the first point across the sequence of the CT projection images. The method can include generating, for a second point along the segment of the coronary artery structure, a corresponding second time attenuation sequence representing the intensity of the second point across the sequence of the CT projection images. The method can include determining, using the first time attenuation sequence associated with the first point along the segment of the coronary artery structure, a first cumulative sum of intensities of the first point across a first time interval. The method can include determining, for the second point along the segment of the coronary artery structure using the second time attenuation sequence, a second time interval across which a second cumulative sum of intensities of the second point matches the first cumulative sum. The method can include determining an arterial flow velocity value representing arterial flow velocity between the first and second points along the segment of the coronary artery structure as a distance between the first and second points along the segment of the coronary artery structure divided by a difference between the first and second time intervals.

DETAILED DESCRIPTION

Four-dimensional (4D) CT digital subtraction angiography (DSA) is an angiographic technique that can be implemented on conventional CT scanners, and that can allow for estimation of arterial flow information, such as arterial flow velocity or arterial flow rate. For the purpose of estimating arterial flow information, one or more processing techniques can be implemented to improve the accuracy and robustness of estimated arterial flow information. One technical problem associated with estimating or determining arterial flow information is the overlap of signals from the left ventricle (e.g., when being filled), which is often superimposed on arterial flow signals from the coronary arteries in the acquired angular projections. In the current disclosure, a process for eliminating or reducing background signal interference in arterial flow signals is described.

Also, in the current disclosure, several approaches for determining fluid flow velocity or fluid flow rate are described. These approaches can involve integrating, or summing, intensities or weighted intensities for points along a segment of a coronary artery structure. These approaches can provide flexibility with regard to time intervals (or time windows) over which the integrations can be performed. Such flexibility leads to reduced complexity and increased estimation robustness and accuracy.

Figure 1:
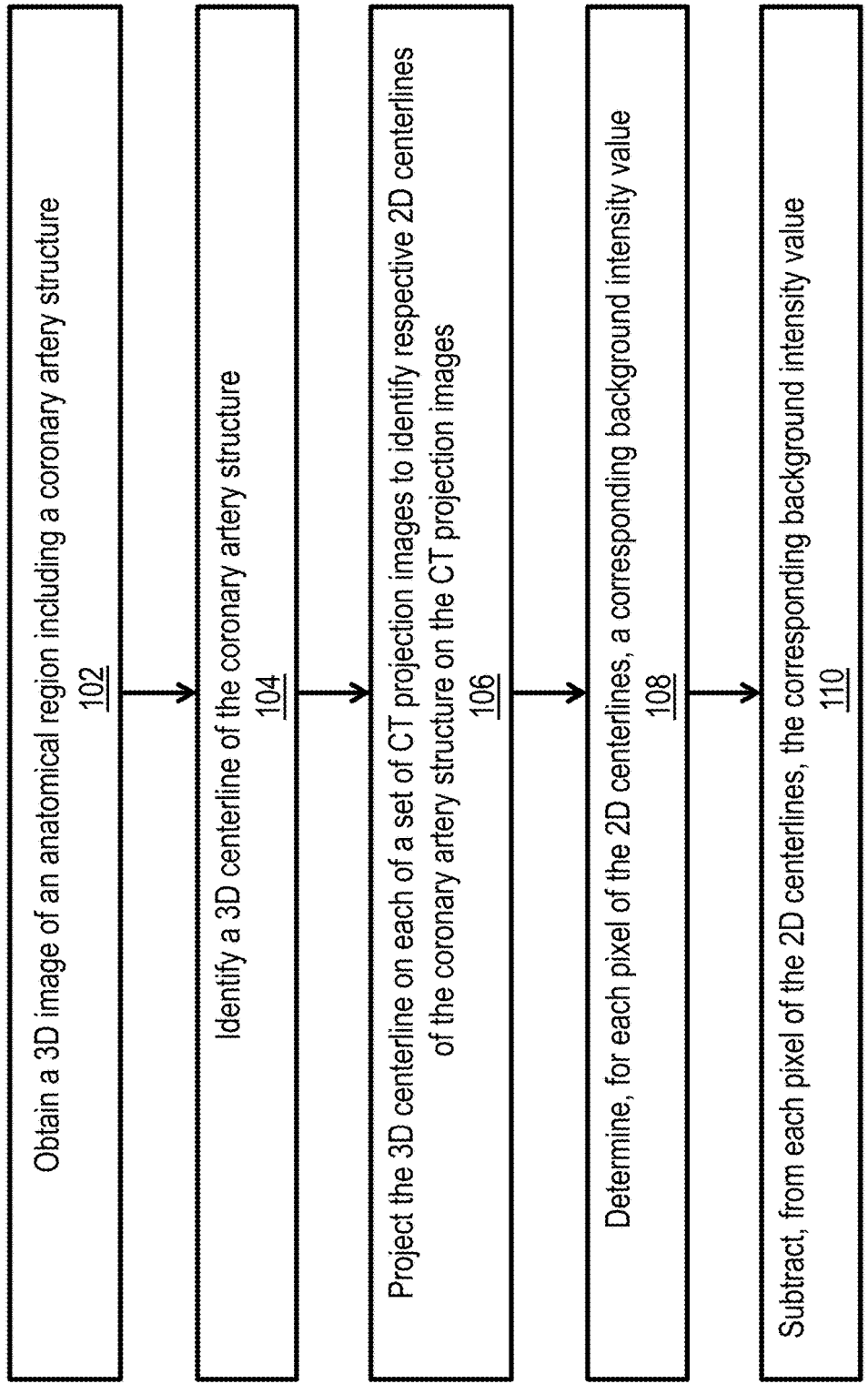
FIG. 1 is a flowchart illustrating a method of generating blood flow signals in coronary arteries, or vessels in general, based on computed tomography projections, according to inventive concepts of this disclosure.

FIG. 1 is a flowchart illustrating a method 100 of generating blood flow signals in coronary arteries, or vessels in general, based on computed tomography projections, according to inventive concepts of this disclosure. The method 100 can include obtaining a three-dimensional (3D) image of an anatomical region including a coronary artery structure (ACT 102). The method 100 can include identifying a 3D centerline of the coronary artery structure using the 3D image of the anatomical region (ACT 104). The method 100 can include projecting the 3D centerline on each CT projection image of a set of CT projection images to identify one or more respective two-dimensional (2D) centerlines of the coronary artery structure on the CT projection image (ACT 106). The method 100 can include determining, for each pixel of the 2D centerlines of the coronary artery structure, a corresponding background intensity value (ACT 108), and subtracting the corresponding background intensity value from the pixel intensity to generate arterial pixel intensity values along the 2D centerlines of the coronary artery structure with mitigated background interference (ACT 110).

The method 100 can be implemented by a CT scanner, a computing device such as a computing device communicatively coupled to the CT scanner, or a combination thereof. For instance, the method 100 can be implemented as computer code instructions that can be stored in a memory and executed by one or more processors associated with the CT scanner, the computing device, or both. A doctor (or other healthcare provider) can place a patient in the CT scanner and inject a contrast agent into a vein of the patient (e.g., in the patient arm). The CT scanner can acquire a plurality of CT projection images, e.g., during multiple gantry rotations, of an anatomic region of the patient while the contrast agent propagates into the patient's blood stream. The CT scanner may acquire the plurality of CT projection images with fixed gantry position. For example, a dual source CT scanner may first perform a prior helical CTA scan to generate a 3D vessel mask, and then acquire the plurality of CT projection images with fixed gantry position. The anatomic region can include a coronary artery structure having one or more coronary artery branches. The CT scanner can start the acquisition of CT projection images immediately after the injection of the contrast agent or at some time instance prior to the injection of the contrast agent. The acquisition of CT projection images can be initiated manually, for example, by a radiology technician, or automatically upon automatic detection of the contrast agent injection. The acquisition of CT projection images can continue for a time duration long enough for the contrast agent to reach and propagate through the whole coronary structure or all the blood vessels of the patient. The time duration may be predefined based on previously acquired historical or statistical data of CTA.

The CT scanner can acquire the plurality of projection images at various projection angles as the CT scanner's gantry rotates around the patient's body or the anatomical region imaged. Each projection image of the plurality of projection images can be associated with a corresponding acquisition time. In some implementations, the CT scanner can have two (or more) x-ray source-detector pairs oriented at an angle (e.g., 90 degrees) relative to each other. The two (or more) x-ray source-detector pairs can acquire simultaneously two (or more) CT projection images at each acquisition time instance of a plurality of acquisition time instances. The CT scanner or a computing device communicatively coupled to the CT scanner can generate one or more 3D images of the coronary artery structure of the anatomical region including the coronary artery structure using the plurality of the CT projection images or a subset thereof. For instance, the CT scanner or a computing device can use a set of CT projection images associated with multiple projection angles to construct a corresponding 3D CT image.

The method 300 can include the one or more processors obtaining the 3D image of the coronary artery structure or the anatomical region including the coronary artery structure (ACT 102). Obtaining the 3D image can include the one or more processors generating the 3D image or retrieving the 3D image from a memory associated with the CT scanner or the computing device. Generating the 3D image can include generating the 3D image in real time or near real time (e.g., immediately after acquisition of the plurality of CT projection images). In some implementations, the one or more processors can generate the 3D image at a later time after the acquisition of the CT projection images (e.g., minutes or hours later). In some implementations, the one or more processors may acquire the 3D image from the CT scanner or from a memory storing the 3D image.

The method 100 can include the one or more processors identifying a 3D centerline of the coronary artery structure using the 3D image of the anatomical region (ACT 104). Identifying the 3D centerline of the coronary artery structure can include marking voxels defining the 3D centerline in the 3D image, or constructing the 3D centerline of the coronary artery structure (e.g., constructing a 3D mask image of the 3D centerline) based on the 3D image of the coronary artery structure. The one or more processors can identify the 3D centerline of the coronary artery structure by discarding, removing, or stripping voxels or layers of the coronary artery structure in the 3D image as if to reduce a thickness of the coronary artery structure. For instance, the one or more processors can use a thinning algorithm approach to erode the coronary artery structure (from the exterior inwards) until only the corresponding centerline is left. The 3D centerline of the coronary artery structure can be one voxel thick. In other words, the one or more processors can erode the coronary artery structure until only a one-voxel-thick skeleton or core of the coronary artery structure remains. In some implementations, the 3D centerline can be more than one voxel thick. The one or more processors may use a surface-based approach to identify the 3D centerline. When using a surface-based approach, the one or more processors can fit maximally inscribed spheres in the coronary artery structure (or segments thereof). The points defining the centers of the spheres can form the 3D centerline of the coronary artery structures.

Figure 2:
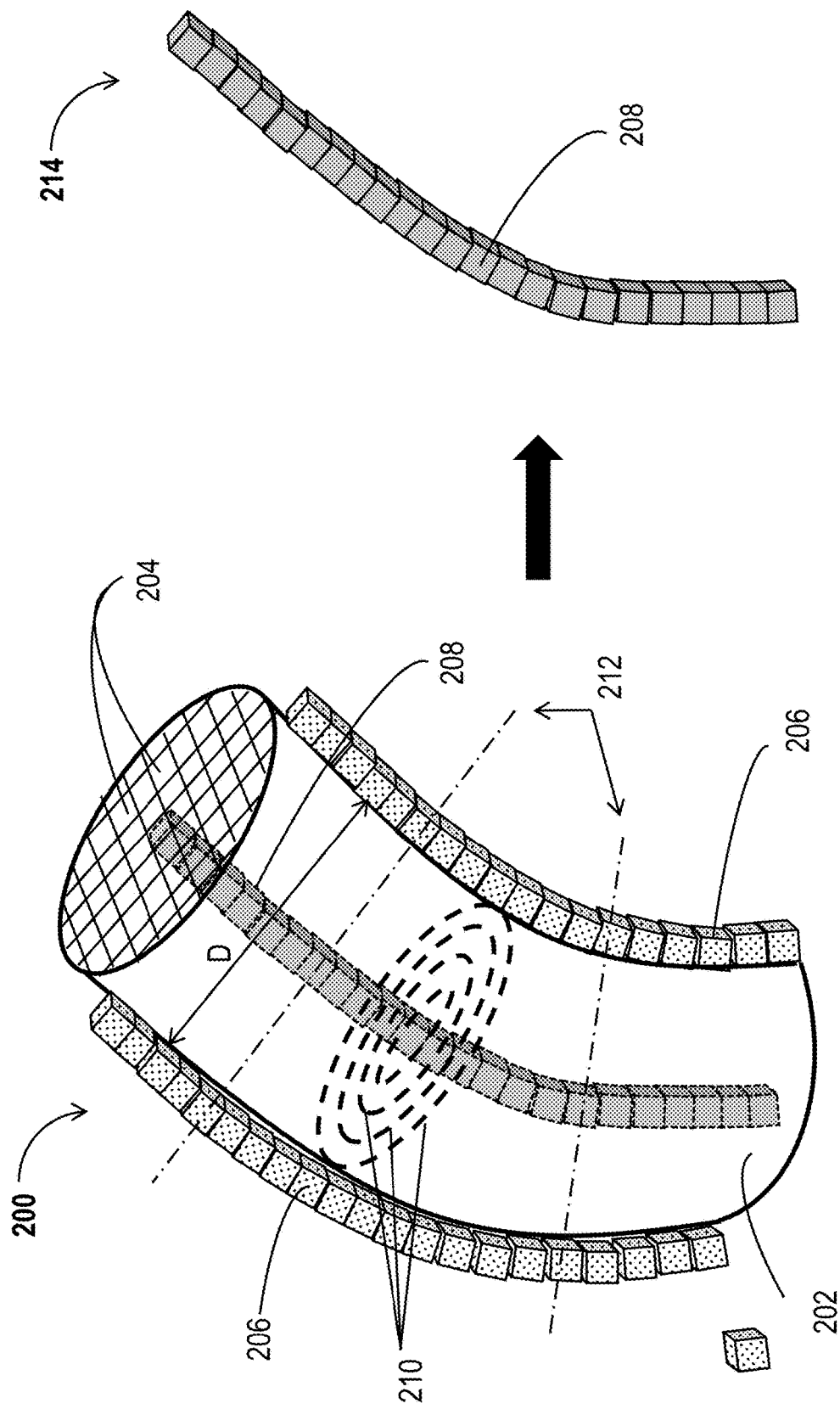
FIG. 2 is a diagram illustrating a visual depiction of an example approach of identifying a 3D centerline based on a 3D image of a coronary artery structure (or a portion thereof), according to inventive concepts of this disclosure.

FIG. 2 is a diagram illustrating a visual depiction of an example approach of identifying a 3D centerline based on a 3D image of a coronary artery structure (or a portion thereof), according to inventive concepts of this disclosure. A 3D image 200 can include a 3D representation 202 of a coronary artery structure. The 3D image 200 can be a 3D CT image or a 3D binary image generated based on the 3D CT image. The 3D representation 202 of the coronary artery structure can include a plurality of voxels 204 defining the coronary artery structure. The voxels 206 can represent tissue or organs (e.g., the left ventricle or myocardium) surrounding the coronary artery structure. The voxels 206 may be referred to as background voxels. If the 3D image 200 is a 3D CT image generated using the CT projection images acquired by the CT scanner, the one or more processors can identify the voxels 204 (or distinguish the voxels 204 from the background pixels 206) using 3D image segmentation techniques. For example, the one or more processors can identify the voxels 204 based on intensity and/or contrast compared to the background voxels 206. If the 3D image 200 is a 3D binary image, the voxels 204 can have an intensity value different from that of the background voxels 206. The one or more processors can generate the 3D binary image based on the 3D CT image using 3D image segmentation techniques.

The centerline 208 can be viewed as a subset of the voxels 204 defining a skeleton of the coronary artery structure or the corresponding 3D representation 202. In particular, the centerline 208 can be a single voxel thick skeleton (as shown in FIG. 2) running along center points of transverse cross sections of the coronary artery structure or the corresponding 3D representation 202. To generate the 3D image 214 of the centerline 208, the one or more processors can generate a copy of the 3D image 200, and strip, or discard, layers (or rings) 210 of voxels from the coronary artery structure or the corresponding 3D representation 202 in the 3D image copy until a single voxel is left at each longitudinal level of the coronary artery structure or the corresponding 3D representation 202. Stripping or discarding the layers or rings of voxels can, for instance, include modifying the intensity of such voxels, e.g., to a background intensity value, and setting the intensity of the remaining voxels forming the centerline 208 to a foreground intensity value in the copy 3D image to generate a mask 214 of 3D centerline 208. Stripping or discarding the layers or rings of voxels can include the one or more processors generating and iteratively updating a data structure indicative of which voxels are non-centerline voxels and which voxels are centerline voxels. The generated data structure or the generated 3D mask 214 can be viewed as a representation (or indicator) of the voxels forming the 3D centerline 208. In some implementations, the one or more processors can generate or identify a 3D centerline that is more than one voxel thick (e.g., 2, 3, or 4 voxels thick) or in diameter.

The one or more processors can record, track, monitor or store the number of voxel rings 210 (of the coronary artery structure or the corresponding 3D representation 202) stripped at each longitudinal level of the coronary artery structure or the corresponding 3D representation 202. The number of voxel rings 210 stripped at each longitudinal level of the coronary artery structure or the corresponding 3D representation 202 can be indicative of the distance between a centerline voxel at that longitudinal level and the closest background voxel 206 (that is beyond the coronary artery structure). For example, each of the break-lines 212 passes through a corresponding centerline voxel and the background pixels closest to that centerline voxel at the same longitudinal level. The one or more processors can determine the diameter D(l) of the coronary artery structure (or the corresponding 3D representation 202) at each longitudinal level l as twice the number of voxel rings 210 stripped at the longitudinal level l plus the number of voxels (e.g., 1) defining the thickness of the centerline 208. The one or more processors can determine the distance between each centerline voxel and the closest background voxel 206 as D divided by 2 (i.e., the radius of the coronary artery structure at the corresponding longitudinal level l).

Intensities of voxels in the middle of the coronary artery structure, such as voxels of the centerline 208, suffer less background interference than voxels 204 closer to the surface (or edge) of the coronary artery structure. In fact, x-rays passing through the centerline 208 cross the coronary artery structure by the maximum distance possible, which is equal to the diameter D(l) of the coronary artery structure at a given longitudinal level l, whereas x-rays penetrating the coronary artery structure but not passing through the centerline 208 cross the coronary artery structure by a distance less than the diameter D(l). Hence, the coronary artery structure contributes more to the attenuations associated with the x-rays passing through the centerline 208 than x-rays not passing through the centerline 208. Accordingly, the intensities of the centerline 208 can provide a better representation or estimate of vascular flow signals (or coronary flow signals) compared to non-centerline voxels of the coronary artery structure or the corresponding 3D representation 202.

While the 3D centerline 208 is described a set of voxels in FIG. 2, in general, the 3D centerline can be viewed as a set of points in the 3D space, for example, defining center points of transverse cross sectional areas of segments of the coronary artery structure or center points of maximally inscribed spheres fitted in the coronary artery structure when using a subsurface approach. For instance, in identifying the 3D centerline, the one or more processors can identify the coordinates of the center points in the 3D space. In the following, the terms "voxel" and "point" are used interchangeably in the 3D space.

The method 100 can include the one or more processors projecting the 3D centerline 208 on each CT projection image of a set of CT projection images to identify one or more respective two-dimensional (2D) centerlines of the coronary artery structure on the CT projection image (ACT 106). The one or more processors can project the 3D centerline 208 on each CT projection image of the plurality of projection images acquired by the CT scanner (or a subset thereof), or each CT projection image of the set (or a subset thereof) of CT projection images used to generate the 3D image 200 (shown in FIG. 2). For each CT projection image, the one or more processors can project the 3D centerline 208 along the projection angle used to acquire that CT projection image (and perpendicular to a plane of the CT projection image) for instance. The projection of the 3D centerline 208 on each CT projection image allows the one or more processors to identify pixels defining (or associated with) the centerline of the coronary artery structure in the that CT projection image. The projection image of the 3D centerline 208 in each CT projection image (pixels defining or associated with the centerline of the coronary artery structure) is referred to herein as a 2D centerline of the coronary artery structure in that CT projection image. The one or more processors may register the 3D image 200 of the coronary artery structure and/or the 3D image 214 of the 3D centerline with the corresponding CT projection images. The one or more processors can identify the 2D centerlines in the CT projection images using image registration.

The method 100 can include the one or more processors determining, for each pixel of the 2D centerlines of the coronary artery structure, a corresponding background intensity value (ACT 108). The one or more processors may determine, for each pixel of a 2D centerline in a first CT projection image, the diameter of the coronary artery structure associated with that pixel. For example, the one or more processors can back-project the pixel onto the 3D centerline image 214 or the 3D image 200 of the coronary artery structure (or use registration of the 3D image of the coronary artery structure with corresponding CT projection images) to identify a centerline voxel corresponding to that pixel, and identify the diameter D(l) corresponding to (or associated with) the centerline voxel. The one or more processors can identify one or more background intensities of one or more background voxels 206 using the diameter D(l) or the radius $$\frac{D(l)}{2}$$

(e.g., background voxels 206 away from the identified centerline voxel by a distance equal to $$\frac{D(l)}{2}).$$

The distance between each centerline voxel and background voxels 206 can be greater than or equal to the radius $$\frac{D(l)}{2}.$$

The centerlines 212 in FIG. 2 illustrates examples of centerline voxels and corresponding background voxels 206 spatially separated or spaced by a distance equal to $$\frac{D(l)}{2}.$$

The one or more processors can determine the background intensity value(s) from the 3D image 200 of the coronary artery structure (if it is a 3D CT projection image) or from one or more CT projection images. For instance, the one or more processors can use the diameter D(l) (or the radius $$\frac{D(l)}{2})$$

to identity one or more background pixels (e.g., pixel(s) located or disposed away from the 2D centerline pixel by a distance equal to $$\frac{D(l)}{2})$$

in the first CT projection image. The one or more processors may identify one or more background pixels in, for example, a second CT projection image acquired simultaneously with the first CT projection image (e.g., when CT scanner has two x-ray source-detector pairs) and at a projection angle different from (e.g., perpendicular to) the projection angle of the first CT projection image. The one or more processors may use a projection of the 3D centerline 208 on the second CT projection image (or using the 3D to 2D image registration) and the diameter D(l) to identify one or more background pixels in the second CT projection image. The one or more processors can determine the intensity value(s) of the one or more background pixels in the second CT projection image. The one or more processors can determine the background intensity value corresponding to the 2D centerline pixel in the first CT projection image as an average background intensity value, a minimum background intensity value, a maximum background intensity value, or other background intensity value associated with one or more identified background voxels 206 (in the 3D image 200) or identified background pixels (in one or more CT projection images).

The method 100 can include the one or more processors subtracting the corresponding background intensity value from the pixel intensity to generate arterial pixel intensity values along the 2D centerlines of the coronary artery structure with mitigated background interference (ACT 110). The one or more processors can subtract from each 2D centerline pixel in each CT projection image the corresponding background intensity value (e.g., subtract away an average, minimum or maximum background intensity value, or a portion of the one or more background intensities associated of the background voxel(s) or background pixel(s) corresponding to the 2D centerline pixel). The subtraction can be applied to each 2D centerline pixel in each of the CT projection images. The subtraction allows for reduction or mitigation of background interference in the intensities of the 2D centerline pixels, therefore, providing an improved estimate or representation of vascular (or arterial) flow signals.

The one or more processors may generate arterial pixel intensity values along the 2D centerlines of the coronary artery structure by using subtraction of mask images. For instance, the CT scanner may acquire one or more mask images prior to contrast injection and subtract from each of the plurality of CT projection images a mask image of the one or more mask images. Mask image subtraction eliminates or mitigates background signal interference with arterial signals. The CT scanner may acquire a plurality of mask images, for example, associated with different respiratory states. The one or more processors may select, for each CT projection image of the plurality of CT projection images, the mask image that is most similar to (or associated with the same respiratory state as) the CT projection image to mitigate motion artifacts. The one or more processors In the case where CT projection images are acquired using a dual source CT scanner, the one or more processors may assign to each 2D centerline pixel an intensity value based on (e.g., minimum or mean intensity among) corresponding intensities in a pair of CT projection images acquired simultaneously using the dual source. The use of intensities from each pair of simultaneously acquired CT projection images to determine 2D centerline pixel intensities can be employed to mitigate signal interference from other structures such as the left ventricle. In generating the arterial pixel intensity values along the 2D centerlines, the one or more processors may use a combination of background subtraction, mask image subtraction, and combining of pairs of CT projection images acquired using the dual source.

In some embodiments, the one or more processors may obtain two or more 3D images (at ACT 102) of the coronary artery structure (or the anatomical region), such that each 3D image is associated with a respective state of a plurality of states of the coronary artery structure. For example, a first 3D image of the coronary artery structure may be associated with a cardiac diastolic (or end-diastolic) phase, and generated using a corresponding first set of CT projection images. A second 3D image of the coronary artery structure may be associated with a cardiac systolic phase for instance, and generated using a corresponding second set of CT projection images. The one or more processors can perform the ACTs 104-110 for the first 3D image of the coronary artery structure (and the corresponding first set of CT projection images), and repeat the same ACTs 104-110 for the second 3D image of the coronary artery structure (and the corresponding second set of CT projection images) to generate two 3D centerlines and two sets of improved vascular flow signals (with subtracted background intensities).

In some embodiments, the CT scanner can acquire a first set of CT projection images prior to injecting the patient with a vasodilator drug, and acquire a second set of CT projection images after injecting the patient with the vasodilator drug. The vasodilator drug causes blood vessels of the patient to dilate. The one or more processors can generate, for each of the sets of CT projection images, a corresponding 3D image of the coronary artery structure. The one or more processors can apply the method TOO to both of the generated 3D images of the coronary artery structure to generate two different sets of improved vascular (or arterial) flow signals (with background signal subtraction) associated with pre-dilation and post dilation, respectively. A comparison of results from pre-dilation and post dilation can be indicative of the presence or absence of one or more medical conditions.

Figure 3:
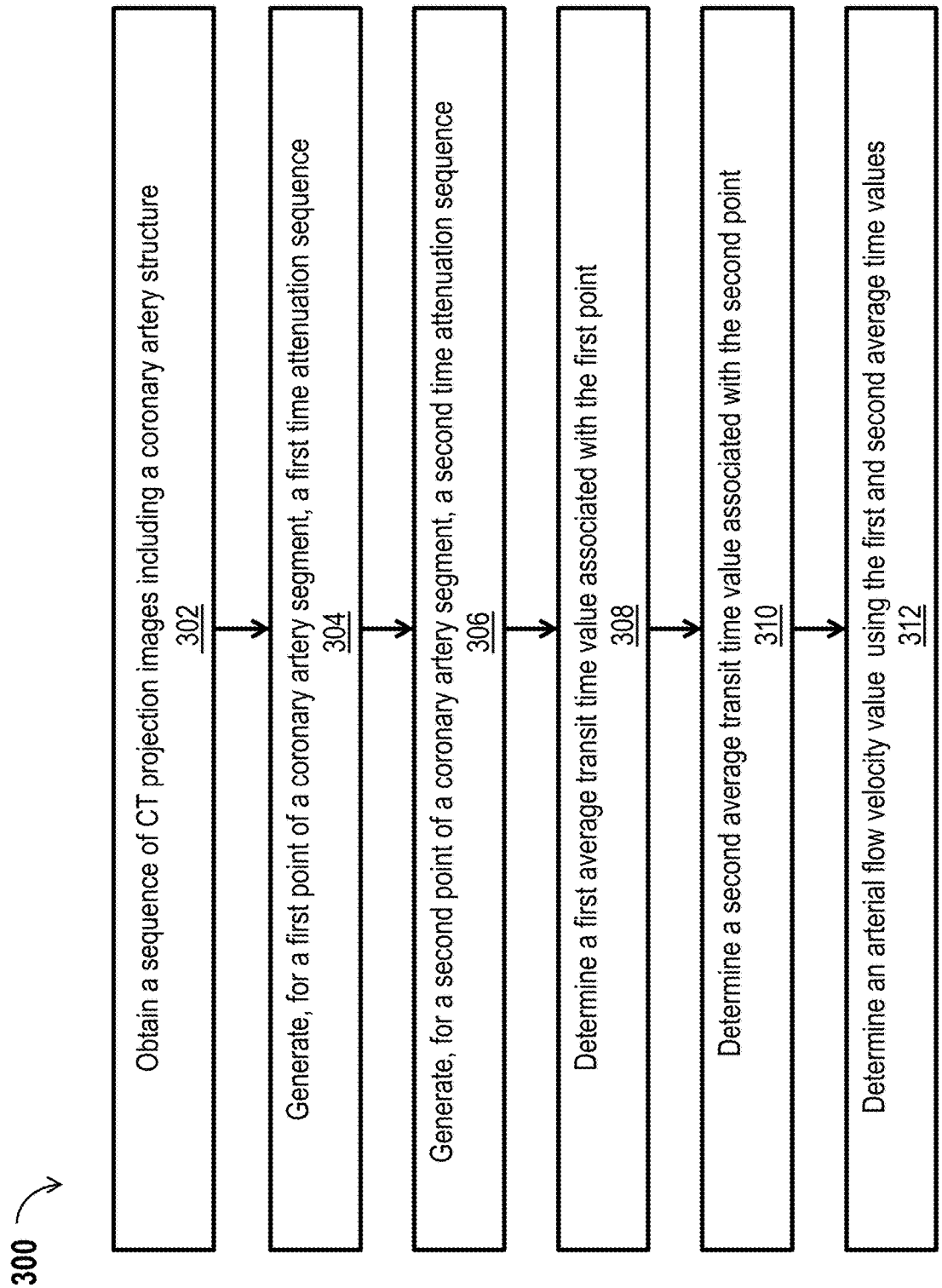
FIG. 3 shows a flowchart illustrating a method of estimating arterial flow (or vascular) velocity based on computed tomography (CT) projections, according to inventive concepts of this disclosure.

FIG. 3 is a flowchart illustrating a method 300 of estimating arterial flow (or vascular) velocity based on computed tomography (CT) projections, according to inventive concepts of this disclosure. The method 300 can include obtaining a sequence of CT projection images of an anatomical region including a coronary artery structure (ACT 302). The method 300 can include generating, for a first point along a segment of the coronary artery structure, a corresponding first time attenuation sequence representing intensity values of the first point across the sequence of the CT projection images (ACT 304), and generating, for a second point along the segment of the coronary artery structure, a corresponding second time attenuation sequence representing intensity values of the second point across the sequence of the CT projection images (ACT 306). The method 300 can include determining, using the first time attenuation sequence, a first average transit time representing an average time duration for arterial flow particles to reach the first point along the segment of the coronary artery structure (ACT 308), and determining, using the second time attenuation sequence, a second average transit time representing an average time duration for arterial flow particles to reach the second point along the segment of the coronary artery structure (ACT 310). The method 300 can include determining an arterial flow velocity value between the first and second points along the segment of the coronary artery structure using the first and second average transit times (ACT 312).

The method 300, similar to method 100, can be implemented by a CT scanner, a computing device such as a computing device communicatively coupled to the CT scanner, or a combination thereof. For instance, the method 300 can be implemented as computer code instructions that can be stored in a memory and executed by one or more processors associated with the CT scanner, the computing device, or both.

The method 300 can include the one or more processors obtaining a sequence of computed tomography (CT) projection images of an anatomical region including a coronary artery structure. As discussed above with regard to FIG. 1, a doctor (or other healthcare provider) may place a patient in the CT scanner and inject a contrast agent into a vein of the patient (e.g., in the patient arm), and the CT scanner can acquire a plurality of CT projection images, e.g., during multiple gantry rotations, of an anatomic region of the patient while the contrast agent propagates into the patient's blood stream. The CT scanner can start the acquisition of CT projection images immediately after the injection of the contrast agent or at some time instance prior to the injection of the contrast agent. The acquisition of CT projection images can be initiated manually, for example, by a radiology technician, or automatically upon automatic detection of the contrast agent injection. The acquisition of CT projection images can continue for a time duration long enough for the contrast agent to reach and propagate through the whole coronary structure or all the blood vessels of the patient. The time duration may be predefined based on previously acquired historical or statistical data of CTA. The CT scanner can acquire the plurality of projection images at various projection angles as the CT scanner's gantry rotates around the patient's body. Each projection image of the plurality of projection images can be associated with a corresponding acquisition time. In some implementations, the CT scanner can have two (or more) x-ray source-detector pairs oriented at an angle (e.g., 90 degrees) relative to each other. The two (or more) x-ray source-detector pairs can acquire simultaneously two (or more) CT projection images at each acquisition time instance of a plurality of acquisition time instances.

The one or more processors can segment the CT projection images to identify pixels (or pixel regions) defining the coronary artery structure in each of the CT projection images. The one or more processors may register the CT projection images with each other. The one or more processors may isolate the pixel regions defining the coronary artery structure in each of the CT projection images and use the isolated pixel regions in the CT projection images to generate one or more 3D images of the coronary artery structure. The one or more processors may register the one or more 3D images of the coronary artery structure with the CT projection images.

The method 300 can include the one or more processors generating, for a first point along a segment of the coronary artery structure, a corresponding first time attenuation sequence representing intensity values of the first point across the sequence of the CT projection images (ACT 304), and generating, for a second point along the segment of the coronary artery structure and different than the first point, a corresponding second time attenuation sequence representing intensity values of the second point across the sequence of the CT projection images (ACT 306). The one or more processors can select the first and second points, for example, to be associated with different longitudinal levels of the coronary artery structure (or the segment thereof). The one or more processors may select the first and second points to be along (or close to) a centerline of a segment of the coronary artery structure, or along a core (e.g., interior region of the segment with more than one voxel in diameter) of the segment. For instance, the one or more processors can identify 2D centerlines of the coronary artery structure in each of the CT projection images as discussed above with regard to at least FIG. 1. Specifically, the one or more processors can identify the 3D centerline 208 of the coronary artery structure based on a generated 3D image (e.g., 3D image 200) of the coronary artery structure as discussed above with regard to FIGS. 1 and 2. The one or more processors can register the 3D image of the coronary artery structure or the identified 3D centerline with the CT projection images. The one or more processors can identify the 2D centerlines of the coronary artery structure in each of the CT projection images based on the registration of the 3D image of the coronary artery structure with the CT projection images or projecting back the 3D centerline on the CT projection images. In some implementations, the one or more processors may select the first and second points to be along the segment of the coronary artery structure (e.g., not necessarily along the corresponding centerline) at two different longitudinal levels.

For each of the first and second points, the one or more processors can identify the corresponding pixels across the sequence of CT projection images using image registration among the sequence of CT projection images, or registration of the 3D image of the coronary artery structure or the 3D centerline with the sequence of CT projection images. For instance, the one or more processors can identify a first sequence of pixels corresponding to the first point across the sequence of CT projection images, and identify a second sequence of pixels corresponding to the second point across the sequence of CT projection images. The one or more processors can generate the first time attenuation sequence as the sequence of intensity values of the first sequence of pixels corresponding to the first point, and generate the second time attenuation sequence as the sequence of intensity values of the second sequence of pixels corresponding to the second point.

The intensity values of the first sequence of pixels and the intensity values of the second sequence of pixels can be adjusted intensities with background interference removed. In particular, for each pixel in the first and second sequences of pixels, the one or more processors can subtract from the corresponding pixel intensity value a respective background intensity value to remove or mitigate background signal interference, and use the adjusted intensity values to generate the first and second time attenuation sequences. The one or more processors may process the CT projection images as discussed above with regard to FIGS. 1 and 2 (in particular ACT 110 of FIG. 1), such that for each pixel associated with the 2D centerlines in the CT projection images, a corresponding background intensity value is subtracted therefrom. The one or more processors can select the first and second points as centerline points, and use the corresponding intensity values (across the set of CT projection images) as computed, or adjusted, in ACT 110 of FIG. 1 to generate the first and second time attenuation sequences.

The method 300 can include the one or more processors determining, using values of the first time attenuation sequence within a time window, a first average transit time value representing an average time duration for arterial flow particles to reach the first point along the segment of the coronary artery structure (ACT 308). The time window determines points (or values) of the first time attenuation sequence that are to be used in determining or computing the first average transit time value. Specifically, the one or more processors can use the points (or values) of the first time attenuation sequence within the time window to determine the first average transit time value. The one or more processors can determine (or compute) the first average transit time value $Tr(p_1)$ for the first point $p_1$ as $$Tr(p_1) = \frac{\int_0^W t \cdot I_1(t)dt}{\int_0^W I_1(t)dt} = \frac{\sum_{t_k \in W} t_k \cdot I_1(t_k)}{\sum_{t_k \in W} I_1(t_k)}, \quad (1)$$

where W is the time window, t represents continuous acquisition time, and $t_k$ represents discrete acquisition time. Specifically, each $t_k$ value can represent a time instance at which a corresponding CT projection image (e.g., $k^{th}$ CT projection image) was acquired by the CT scanner. The function $I_1(t_k)$ can represent the first time attenuation sequence and the function $I_1(t)$ can represent the corresponding continuous time attenuation function. Each time attenuation value $I_1(t_k)$ can represent the intensity of the first point at the $k^{th}$ CT projection image. In computing the first average transit time value $Tr(p_1)$, the one or more processors can use time attenuation values (or intensities of the first point $p_1$) $I_1(t_k)$ associated with CT projection images having acquisition time values $t_k$ within the time window W.

The method 300 can include the one or more processors determining, using values of the second time attenuation sequence within the time window, a second average transit time value representing an average time duration for arterial flow particles to reach the second point along the segment of the coronary artery structure (ACT 310). The one or more processors can use the same time window as that used to determine or compute the first average transit time value. The one or more processors can determine (or compute) the second average transit time value $Tr(p_2)$ for the second point $p_2$ as $$Tr(p_2) = \frac{\int_0^W t \cdot I_2(t)dt}{\int_0^W I_2(t)dt} = \frac{\sum_{t_k \in W} t_k \cdot I_2(t_k)}{\sum_{t_k \in W} I_2(t_k)}, \quad (2)$$

where W is the same time window used in equation (1), the function $I_2(t_k)$ can represent the second time attenuation sequence, and the function h(t) can represent the corresponding continuous time attenuation function. Each time attenuation value $I_2(t_k)$ can represent the intensity of the second point at the $k^{th}$ CT projection image or the $k^{th}$ value in the second time attenuation sequence. A radiologist technician can select, e.g., through manual input, the boundaries of the time window W. The one or more processors can determine the boundaries of the time window W, for example, based on processing of the first time attenuation sequence $I_1(t_k)$ the second time attenuation sequence $I_2(t_k)$, or both. For instance, the radiologist technician or the one or more processors may select the time window W to start after contrast injection and end before a saturation zone associated with the first time attenuation sequence $I_1(t_k)$ or the second time attenuation sequence $I_2(t_k)$. The one or more processors may use different time windows for computing the first average transit time value $Tr(p_1)$ and the second average transit time value $Tr(p_2)$. For instance, the one or more processors can use intensity threshold values to determine the time window to be used for each point. However, the use of threshold values increases the computational complexity and may increase errors in the vascular velocity or flow estimates as such estimates depend on the threshold values used.

The method 300 can include the one or more processors determining an arterial (or a vascular) flow velocity using the first average transit time value and the second average transit time value (ACT 312). The one or more processors can determine the distance between the first point and the second point. The one or more processors can determine the distance between both points, for example, as the distance between the corresponding voxels in the 3D image of the coronary artery structure (e.g., 3D image 200) or the 3D image of the centerline (e.g., 3D image 214). The one or more processors may scale the distance between the corresponding voxels by the inverse of a scaling factor (if any) of the CT projection images. The one or more processors can determine (or compute) the difference between the first and second average transit time values, and determine the flow velocity between the first and second points along the segment of the coronary artery structure as the distance between the first and second points divided by the absolute difference between the first and second average time values. That is:

$$V(p_1, p_2) = \frac{d}{|Tr(p_2) - Tr(p_1)|}, \quad (3)$$

where d is the distance between the first point $p_1$ and the second point $p_2$, $V(p_1,p_2)$ is the vascular (or arterial) flow velocity between the points $p_1$ and $p_2$, and $|Tr(p_2)-Tr(p_1)|$ is the absolute difference between the first and second average transit time values. The distance d can be expressed in terms of voxels or in terms of a distance unit (e.g., in inches or centimeters). The absolute difference between the first and second average transit time values can be expressed in terms of a time unit (e.g., seconds).

While the method 300 is described with respect to determining the vascular velocity between a pair of points along a segment of the coronary artery structure, the one or more processors can determine vascular velocities for a plurality of points along one or more segments of the coronary artery structure. For instance, with regard to ACTs 304 and 306 of method 300, the one or more processors can generate, for each point along the centerline of the coronary artery structure (or a segment thereof), a corresponding time attenuation sequence. Also, with regard to ACTs 308 and 310, the one or more processors can determine, for each point along a segment of the coronary artery structure (or a centerline thereof), a corresponding average transit time using equation (1) or (2). Given the average transit time for each point (or voxel) along a segment of the coronary artery structure or along the corresponding centerline (e.g., centerline 208 shown in FIG. 2) and the location of that point (or voxel) along the segment of the centerline, the one or more processors can use linear fitting (e.g., linear least squares regression) to determine a liner function (or line) that fits pairs of data points where each pair of data points is associated with a point (or voxel) along the segment (or the centerline) of the coronary artery structure. Specifically, each pair of data points includes the location of the corresponding point (or voxel) along the segment (or the centerline) and the average transit time for that point. The difference between the locations of any pair of points along the segment or the centerline can represent the distance between the pair of points. The one or more processors can determine the vascular velocity associated with the segment as the inverse of the slope of the linear function or line (e.g., where an x-axis represents the locations of the points along the segment or centerline and a y-axis represents the average transit time).

For each segment (or branch) of the coronary artery structure, the one or more processors can determine the respective arterial flow velocity using linear fitting as described above, or can one or more arterial flow velocities associated with one or more pairs of points along the centerline of that segment. For example, the one or more processors can determine a plurality of arterial flow velocities associated with a plurality of pairs of points along the centerline of the segment. The one or more processors can use the average, median, maximum, or minimum of the plurality of the arterial flow velocities as an estimate of the arterial flow velocity within the segment of the coronary artery structure. The one or more processors can arrange the plurality of the arterial flow velocities associated with the segment into a histogram and use the center velocity of the histogram bin with the highest frequency as an estimate of the arterial flow velocity within the segment of the coronary artery structure. The one or more processors may use the arterial flow velocity between a single pair of points along the centerline of the segment as the arterial flow velocity within the segment.

Figure 4A:
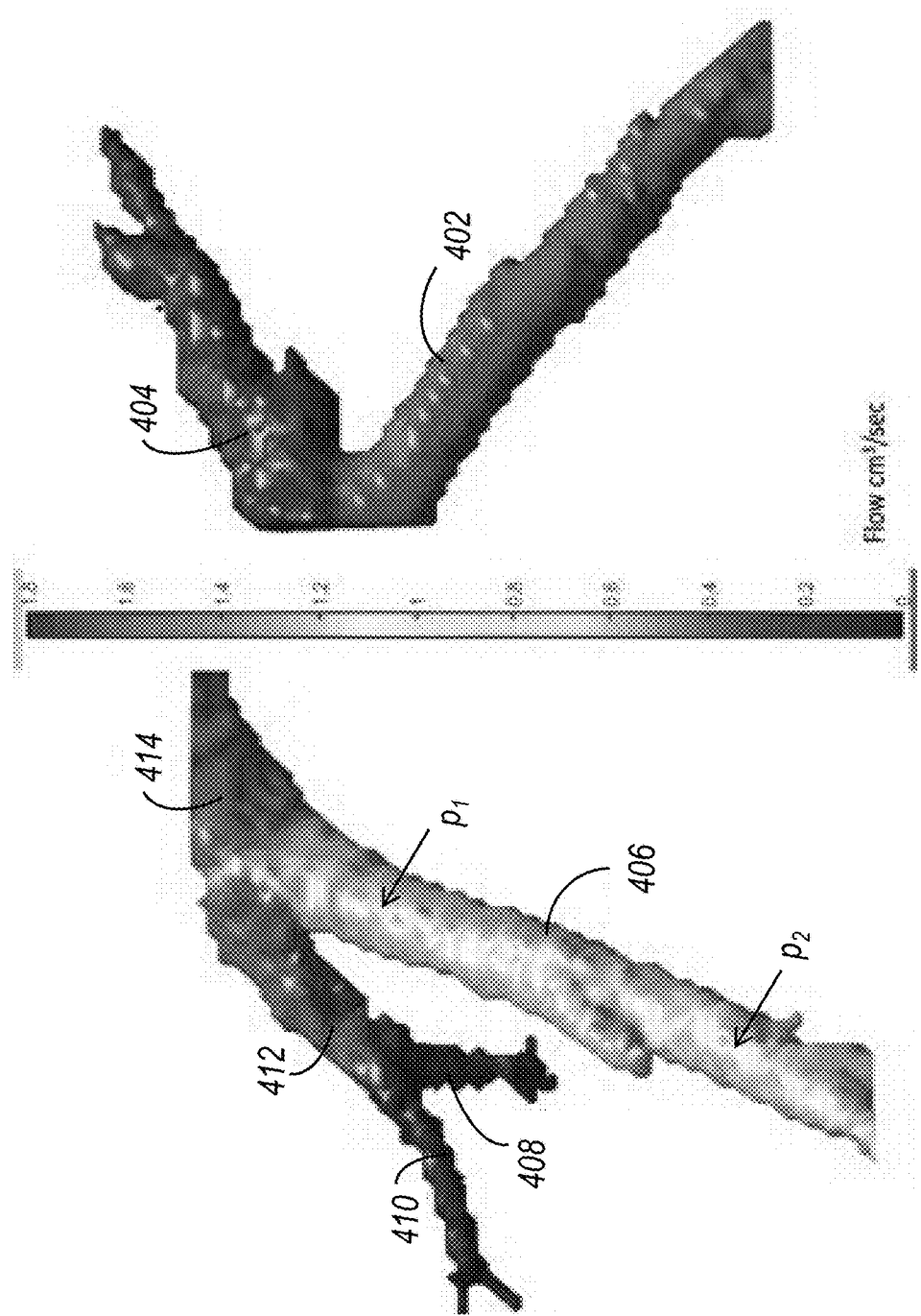
FIG. 4A shows example results depicting vascular flow along a coronary artery structure determined using the method of FIG. 3, according to inventive concepts of the current disclosure.
Figure 4D:
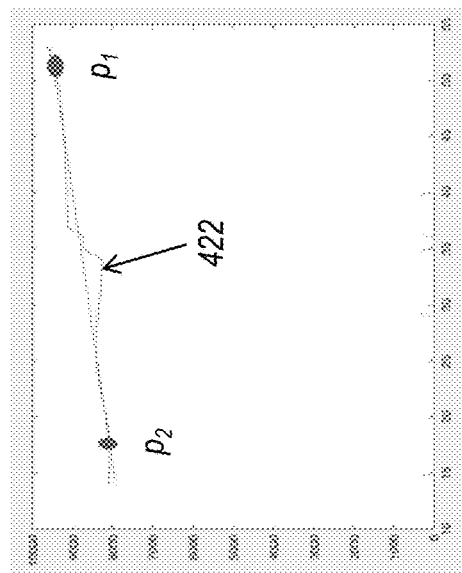
FIG. 4D shows an example curve of average transit time along a portion of a segment of the coronary artery structure between the points $p_1$ and $p_2$, according to inventive concepts of the current disclosure.
Figure 4B:
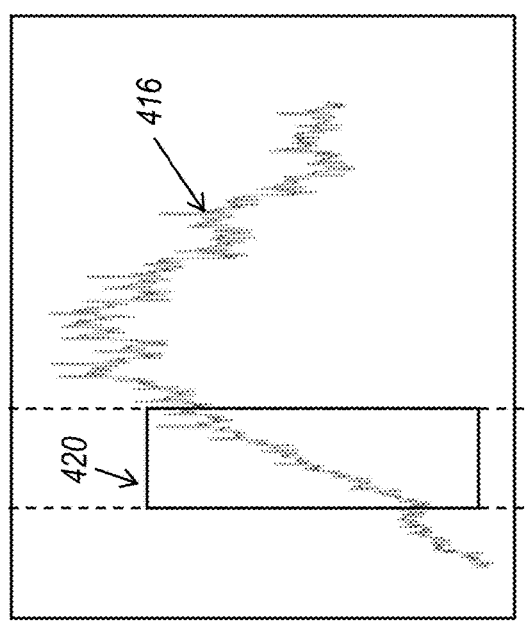
FIGS. 4B and 4C show example time attenuation sequences associated with two points $p_1$ and $p_2$ along a segment of the coronary artery structure of FIG. 4A, according to example embodiments of the current disclosure.
Figure 4C:
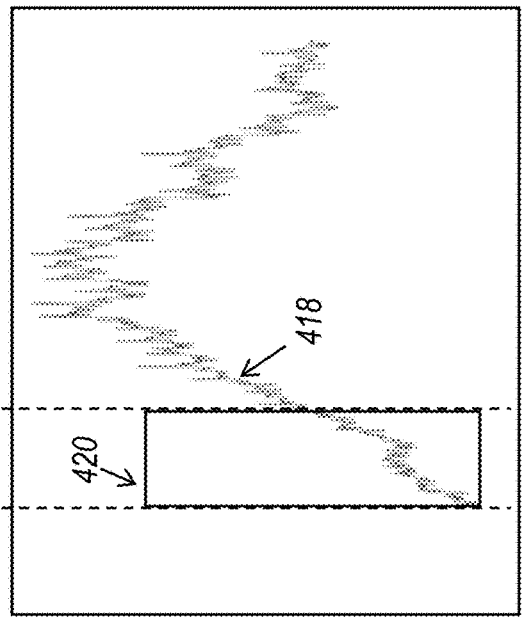

FIGS. 4A-4D show experimental results obtained using the method 300 of FIG. 3, according to inventive concepts of the current disclosure. Specifically, FIG. 4A shows experimental results depicting arterial flow rate within a coronary artery structure 400 of a pig determined using the approach described with regard to FIG. 3. FIGS. 4B and 4C show example time attenuation sequences associated with two points $p_1$ and $p_2$ along a segment of the coronary artery structure of FIG. 4A. FIG. 4D shows an example plot of average transit time along a portion of the segment of the coronary artery structure between the points $p_1$ and $p_2$. Point p1 is a proximal point and point p2 is a distal point.

Referring to FIG. 4A, the coronary artery structure 400 belongs to a pig and includes a plurality of segments (or branches) 402-414. The arterial flow rate within the segments (or branches) 402-414 is color coded. The arterial flow rate shown in FIG. 4A is determined as fluid flow velocity at each segment multiplied by the cross-sectional area of that segment. The arterial flow velocity is determined using the approach described above with regard to FIG. 3. In particular, the centerline of the coronary artery structure is constructed and time attenuation sequences for a plurality of points along the centerline are generated.

FIG. 4B shows the time attenuation sequence 416 for point $p_1$ on segment 406 and FIG. 4C shows the time attenuation sequence 418 for point $p_2$ on the same segment 406. The average transit time for both points (and other points along the centerline) is determined using the integration window 420. Specifically, the integration window 420 is fixed when evaluating both equations (1) and (2) and determining the average transit times for both points $p_1$ and $p_2$ (and other points along the centerline).

FIG. 4D shows a plot 422 of average transit time along a portion of the segment 406 between points $p_1$ and $p_2$. The arterial flow velocity is determined as the inverse of the slope of the line connecting the average transit time value for point $p_1$ to the average transit time value for point $p_2$ in FIG. 4D. The arterial flow velocity between other pairs of points along segment 406 or any of the other segments 402-404 and 408-414 is determined in the same way. The arterial flow velocity for each of the segments 402-414 is multiplied by the cross-sectional area of the corresponding segment to determine the arterial flow rate for the segment. The obtained arterial flow rates for the segments 402-414 are shown in color-coded format in FIG. 4A. The arterial flow rates for the segments 402-414 are, respectively, 1.54, 1.74, 1.03, 0.30, 0.183, 0.47 and 1.45 cm$^3$/sec.

Figure 5:
FIG. 5 shows results for arterial flow rate obtained using the method of FIG. 3, according to inventive concepts of the current disclosure.
Figure 5:
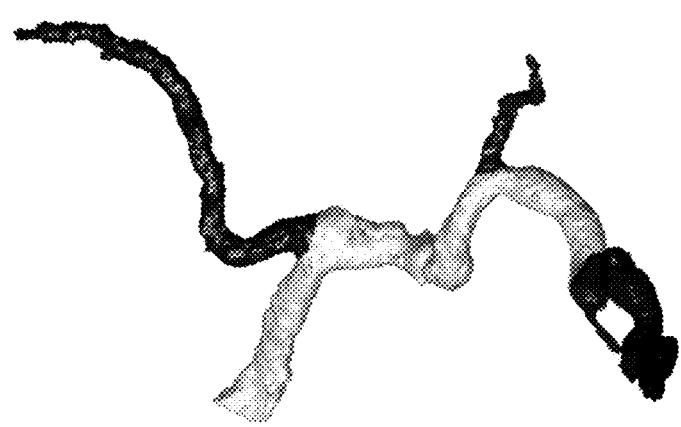
Figure 5:
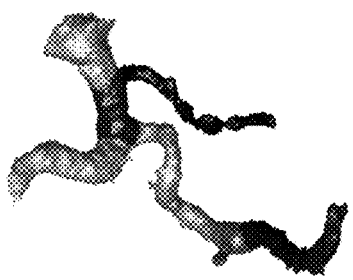

FIG. 5 shows experimental results for arterial flow rate obtained using the method 300 of FIG. 3, according to inventive concepts of the current disclosure. In particular, arterial flow rate values within various branches (or segments) of coronary artery structures of a pig are color coded. The arterial flow rates shown in FIG. 5 are determined (or computed) in a similar way as discussed with regard to FIGS. 3 and 4A-4D. The steps of method 300 are applied to CT projection images of the pig.

Figure 6:
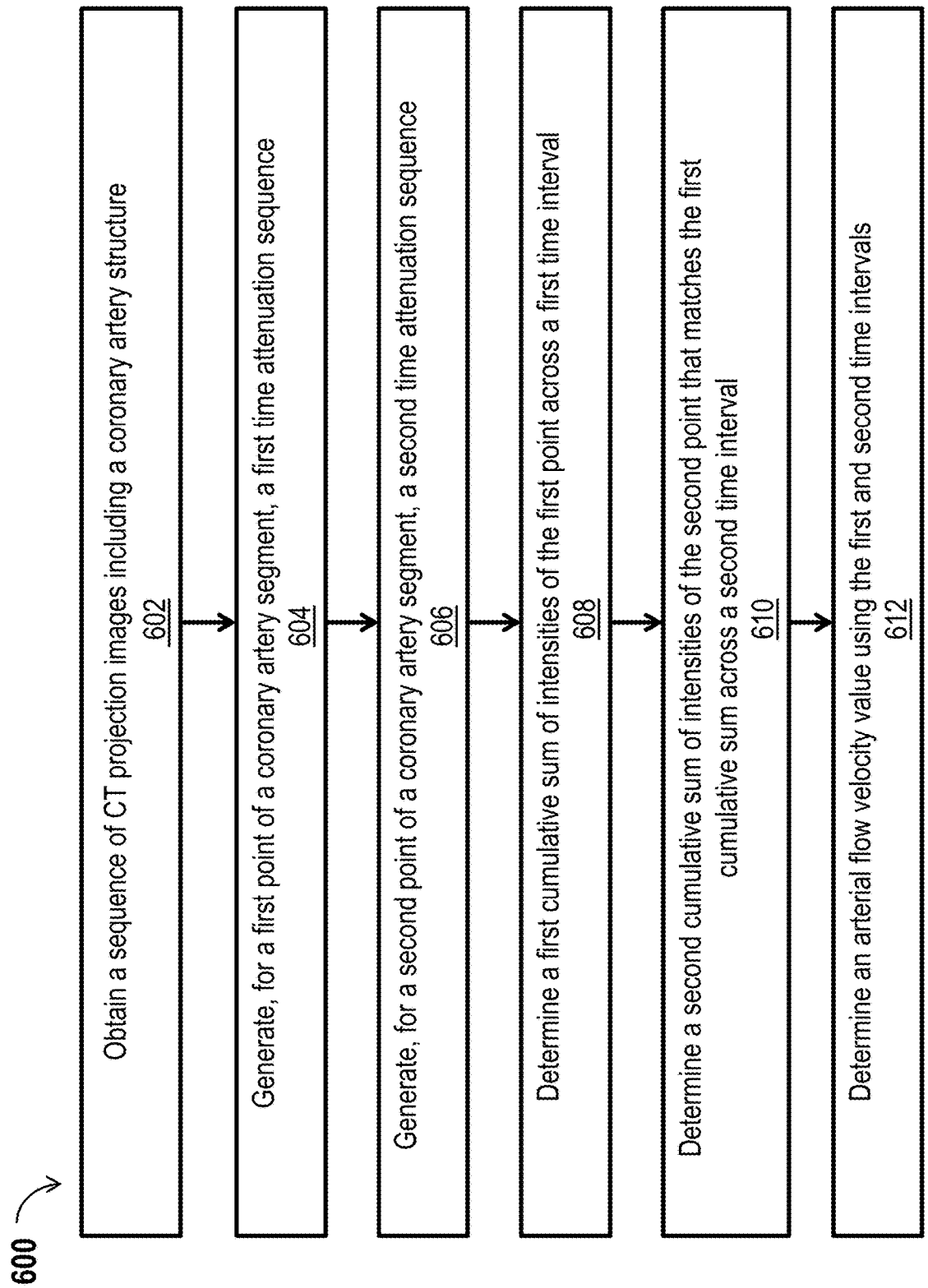
FIG. 6 shows a flowchart illustrating a method 600 of estimating arterial flow (or vascular) velocity based on computed tomography (CT) projections, according to inventive concepts of this disclosure.

FIG. 6 shows a flowchart illustrating a method 600 of estimating arterial flow (or vascular) velocity based on computed tomography (CT) projections, according to inventive concepts of this disclosure. The method 600 can include obtaining a sequence of CT projection images of an anatomical region including a coronary artery structure (ACT 602). The method 600 can include generating, for a first point along a segment of the coronary artery structure, a corresponding first time attenuation sequence representing intensity values of the first point across the sequence of the CT projection images (ACT 604), and generating, for a second point along the segment of the coronary artery structure, a corresponding second time attenuation sequence representing intensity values of the second point across the sequence of the CT projection images (ACT 606). The method 600 can include determining, using the first time attenuation sequence, a first cumulative sum of intensities of the first point across a first time interval (ACT 608), and determining, for the second point along the segment of the coronary artery structure using the second time attenuation sequence, a second time interval across which a second cumulative sum of intensities of the second point matches the first cumulative sum (ACT 610). The method 600 can include determining an arterial flow velocity value representing arterial flow velocity between the first and second points using the first and second time intervals (ACT 612).

The method 600 represents another approach for determining arterial flow velocity (or arterial flow rate) using CT projection images of an anatomical region including a coronary artery structure. With regard to ACT 602, one or more processors associated with the CT scanner can obtain the sequence of CT projection images in a similar way as discussed above with regard to ACT 302 of method 300. Also, the one or more processors can generate the first and second time attenuation sequences (ACTs 604 and 608) in a similar way as discussed above with regard to ACTs 302 and 304 of method 300, respectively. The one or more processors may identify or construct the centerline of the coronary artery structure, e.g., as discussed with regard to FIGS. 1 and 2 above, and generate a corresponding time attenuation sequence for each point (or voxel) along the centerline.

The method 600 can include the one or more processors determining, using the first time attenuation sequence, a first cumulative sum of intensities of the first point across a first time interval (ACT 608). For example, the one or more processors can use a registration of a 3D image of the coronary artery structure, a segment thereof, or the corresponding centerline (e.g., 3D image 200 or 214) to the CT projection images to determine the intensities of the first point along the sequence of CT projection images. The one or more processors can determine the first cumulative sum $CS_1(T_1)$ across a first time interval having time duration $T_1$ as $$CS_1(T_1) = \int_0^{T_1} I_1(t)dt = \Sigma_{t_k \in [0, T_1]} I_1(t_k). \qquad (4)$$

The function $I_1(t)$ and the corresponding discrete sequence $I_1(t_k)$ represent the intensity of the first point over time or across the sequence of CT projection images. The first time interval $[0, T_1]$ is defined as starting at time 0 (e.g., time instance at which contrast injection starts). In some implementations, the first time interval can be can be defined to start at another time instance.

The intensity of the first point at any point of time can be viewed as indicative (or representative) of the number of contrast particles that pass through the first point at that point of time. Similarly, the first cumulative sum $CS_1(T_1)$ across the first time interval $[0, T_1]$ can be viewed as indicative of the total number of contrast particles passing through the first point during the first time interval.

The method 600 can include the one or more processors determining, for the second point along the segment of the coronary artery structure using the second time attenuation sequence, a second time interval across which a second cumulative sum of intensities of the second point matches the first cumulative sum (ACT 610). The one or more processors can determine a second time interval $[0, T_2]$ such that the second cumulative sum $CS_2(T_2)$ of intensities of the second point across the second time interval is equal to the first cumulative sum $CS_1(T_1)$. That is, $$CS_2(T_2) = \int_0^{T_2} I_2(t) dt = \Sigma_{t_k \in [0, T_1]} I_2(t_k) = CS_1(T_1), \quad (5)$$

where the function $I_2(t)$ and the corresponding discrete sequence $I_2(t_k)$ represent the intensity of the second point over time or across the sequence of CT projection images. Similar to the first point, the second cumulative sum $CS_2(T_2)$ can be viewed as indicative (or representative) of the total number of contrast particles passing through the second point during the second time interval $[0, T_2]$. The first and second time intervals can start at the same time instance.

To determine the second time interval, the one or more processors can evaluate the second cumulative sum (e.g., using equation (5)) over various time intervals, and compare the evaluated value of the second cumulative sum to the first cumulative sum until a match is reached. The one or more processors may evaluate the first and second cumulative sums for all (or a plurality of) acquisition time instances $t_k$ (e.g., over the time intervals $[0, t_k]$), and then determine both intervals $[0, T_1]$ and $[0, T_2]$ such that $CS_2(T_2) = CS_1(T_1)$. The one or more processors may evaluate the expression of the second cumulative sum (e.g., as shown in equation (5)) at a later time points compared to $T_1$ to determine the time point $T_2$ at which the second cumulative sum is equal to the first cumulative sum.

Figure 7A:
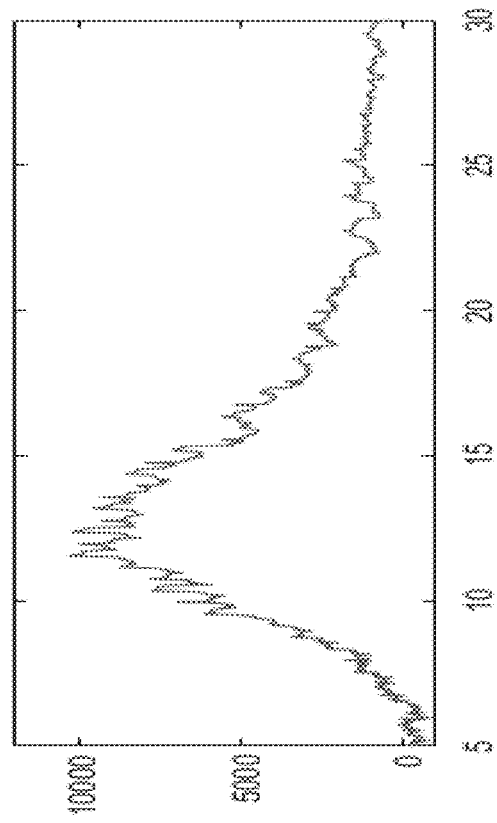
FIGS. 7A-7E show example plots of time attenuation sequences and cumulative sums of intensities for two distinct points $p_1$ and $p_2$ along a segment of a coronary artery structure, according to inventive concepts of the current disclosure.
Figure 7B:
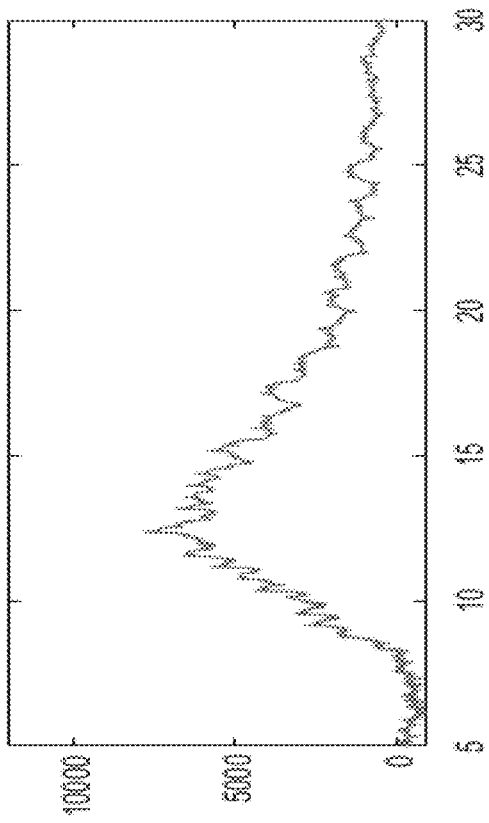
Figure 7C:
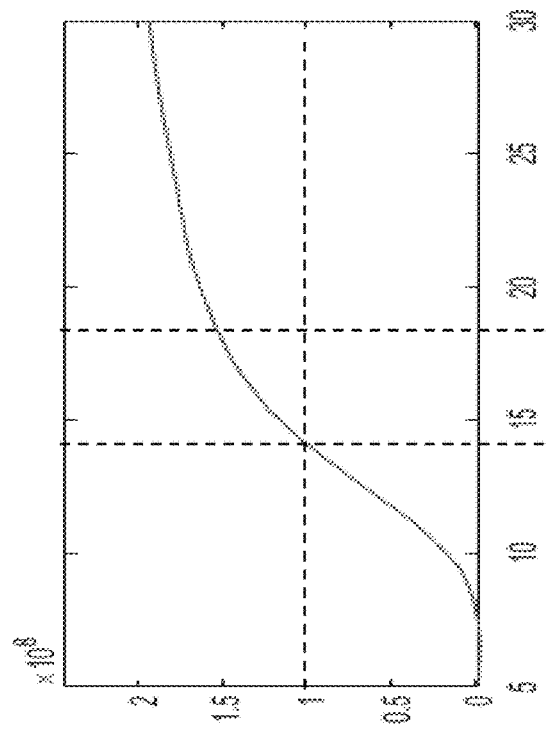
Figure 7D:
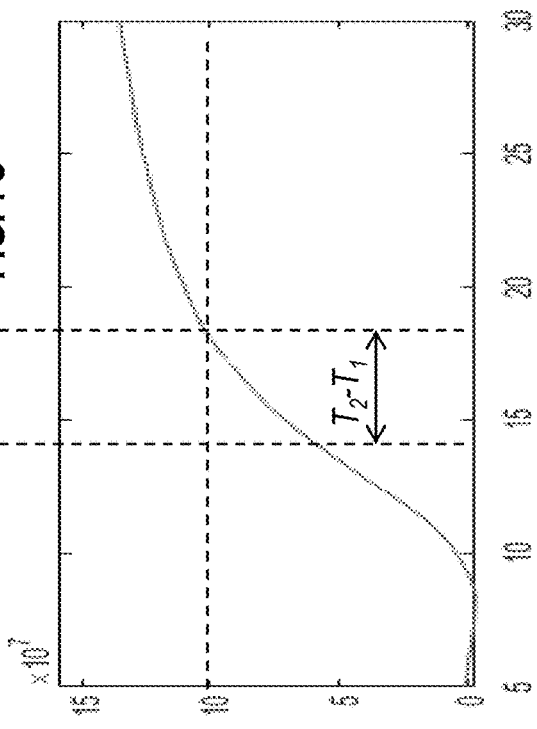
Figure 7E:
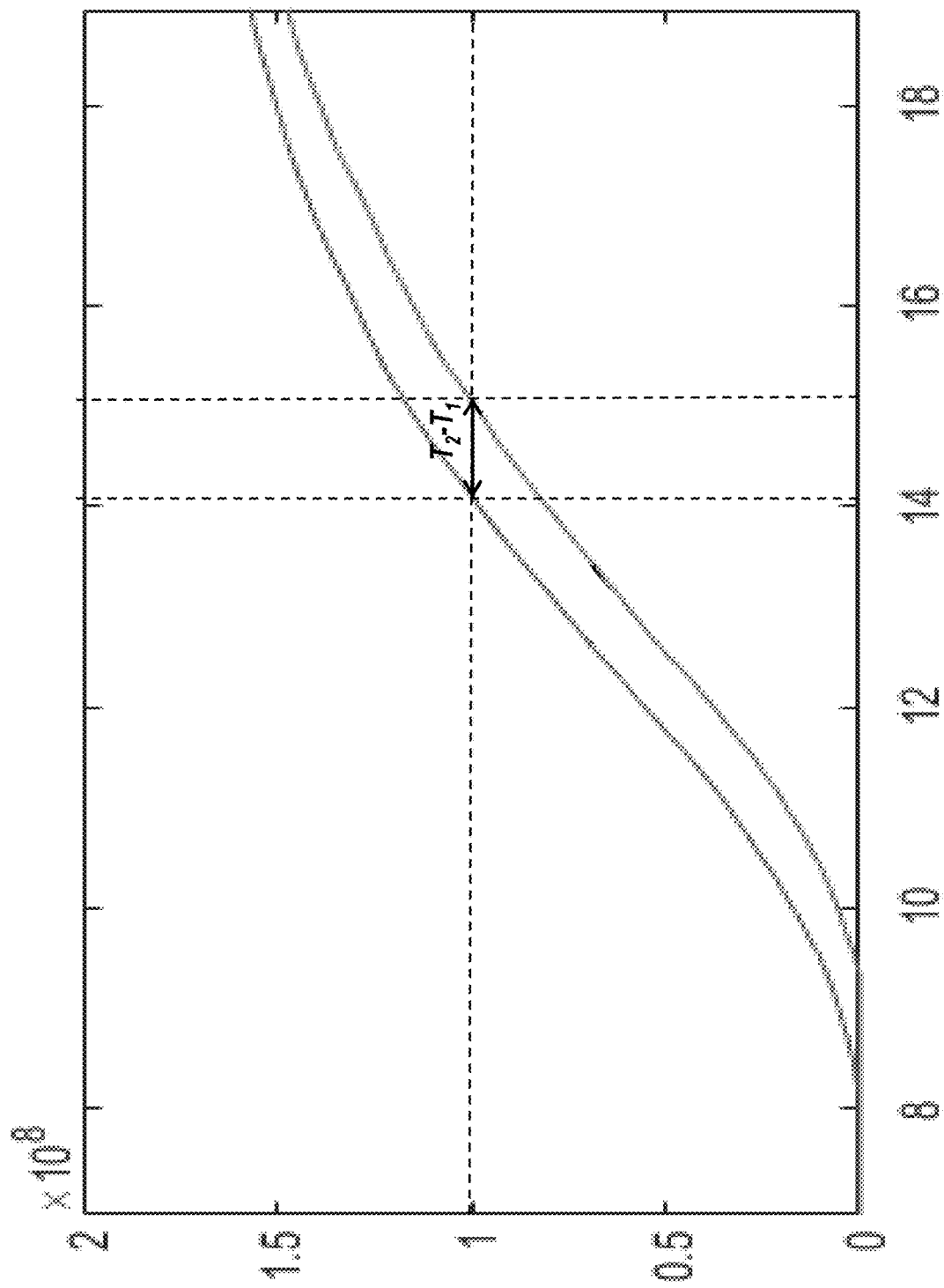

FIGS. 7A-7E show example plots of time attenuation sequences and cumulative sums of intensities for two distinct points $p_1$ and $p_2$ along a segment of a coronary artery structure, according to inventive concepts of the current disclosure. Specifically, FIGS. 7A and 7B show the plots of time attenuation sequences for the points $p_1$ and $p_2$, respectively. FIGS. 7C and 7D show the cumulative sum functions of intensities for the points $p_1$ and $p_2$, respectively, evaluated at various points of time (e.g., points of time corresponding acquisition time instances of CT projection images). FIG. 7E shows both cumulative sum functions of FIGS. 7C and 7D together in one graph. The horizontal dashed lines in FIGS. 7C and 7D indicate a value of $10^8$ for the first and second cumulative sums of intensities. The vertical dashed lines in FIGS. 7C and 7D represent the time values $T_1$ and $T_2$ to, respectively, achieve a first cumulative sum equal to $10^8$ for the first point $p_1$ and a second cumulative sum equal to $10^8$ for the second point $p_2$. The same plots are shown together in FIG. 7E. Using the plots in FIGS. 7C and 7D (or in FIG. 7E), the one or more processors can identify various pairs of time instances $(T_1, T_2)$, and therefore can determine multiple estimates of the arterial flow velocity between the points $p_1$ and $p_2$. The one or more processors may use, for example, the average, median, maximum, or minimum of such estimates as the arterial flow velocity between the points the $p_1$ and $p_2$. The one or more processors may generate a histogram for the determined estimates and use the histogram bin with the highest frequency to determine the arterial flow velocity between the points the $p_1$ and $p_2$.

The method 600 can include the one or more processors determining an arterial flow velocity value representing arterial flow velocity between the first and second points along the segment of the coronary artery structure using the first and second time intervals (ACT 612). The one or more processors can determine the arterial flow velocity between the first and second points as the distance between the first and second points along the segment of the coronary artery structure divided by the difference in time duration between the first and second time intervals. Considering that the first cumulative sum $CS_1(T_1)$ represents the number of contrast particles passing through the first point during the first time interval $[0, T_1]$ and that the second cumulative sum $CS_1(T_1)$ represents the number of contrast particles passing through the second point during the second time interval $[0, T_2]$, then the equality $CS_2(T_2) = CS_1(T_1)$ means that the same number of contrast particles takes a time duration $T_1$ to pass through the first point but takes a time duration $T_2$ to pass through the first point. The difference between the two time durations $T_1$ and $T_2$ can be viewed as representing the time duration taken by the contrast particles to travel from the first point to the second point (if the first point is arranged upstream relative to the second point, or to travel from the second point to the first point if the first point is arranged downstream relative to the second point). Accordingly, the one or more processors can determine (or compute) the velocity of the contrast particles, which is also the arterial flow velocity, as the distance d between the first and second points divided by the absolute difference between the time durations $T_1$ and $T_2$ of the first and second time intervals. That is, $$V(p_1, p_2) = \frac{d}{|T_2 - T_1|}. \quad (6)$$

Similar to ACT 312 of FIG. 3, the one or more processors can use linear fitting to determine the arterial flow velocity associated with the segment of the coronary artery structure. Specifically, For a plurality of points $p_k$, $k=1 \ldots N$, along the segment of the coronary artery structure (or the corresponding centerline), the one or more processors can determine for each point $p_k$ the corresponding location $x_k$ and the corresponding time duration $T_k$ such that $CS(T_1) = CS(T_2) = CS(T_k)$. The one or more processors can determine linear function (or a line) that best fits the pairs of points $(x_k, T_k)$, and determine the vascular velocity associated with the segment of the coronary artery structure as the inverse of the slope of the linear function (or line).

In some embodiments, the CT scanner can acquire a first set of CT projection images prior to injecting the patient with a vasodilator drug, and acquire a second set of CT projection images after injecting the patient with the vasodilator drug. The vasodilator drug causes blood vessels of the patient to dilate. The one or more processors can generate, for each of the sets of CT projection images, a corresponding 3D image of the coronary artery structure. The one or more processors can apply the method 100 to both of the generated 3D images of the coronary artery structure to generate two different sets of improved vascular (or arterial) flow signals (with background signal subtraction) associated with pre-dilation and post dilation, respectively. The one or more processors can apply the method 300 or the method 600 to first and second sets of CT projection images to determine two separate arterial flow velocities (or two arterial flow rates) associated with pre-dilation and post dilation, respectively. The one or more processors or a physician can compare the pre-dilation and post dilatation arterial flow velocities (or rates) to determine abnormalities, if any, associated with the patient. For instance, if the absolute) difference between both pre-dilation and post dilatation arterial flow velocities (or rates) is insignificant, e.g., smaller than a predefined threshold value, that may be indicative of a vascular abnormality.

The one or more processors can generate a first 3D image of the coronary artery structure, associated with a cardiac diastolic (or end-diastolic) phase, using a corresponding first set of CT projection images, and generate a second 3D image of the coronary artery structure, associated with a cardiac systolic phase, using a corresponding second set of CT projection images. The one or more processors can determine separate arterial flow information (e.g., velocities or rates) of one or more segments for each cardiac state or phase, for example, by applying the method 300 or the method 600 to each set of CT projection images (and corresponding 3D image).

When applying the method 600, the one or more processors can identify or construct a 3D centerline of the coronary artery structure (e.g., as discussed with regard to FIGS. 1 and 2), and determine a cumulative sum function of intensities CS(T) (as shown in FIGS. 7C and 7D) for each point along the 3D centerline. The one or more processors can identify multiple pairs of points along the 3D centerline. For each pair of points including a first point and a second point, the one or more processors can determine a first time instance associated with the first point and a second time instance associated with the second point such that the cumulative sum function associated with the first point has a corresponding value at the first time instance that is equal to a value of the cumulative sum function associated with the second point at the second time instance (e.g., as discussed above with regard to FIGS. 7C-7E). The one or more processors can determine the arterial flow velocity for each pair of points using the corresponding pair of time instances and the distance between that pair of points. Accordingly, the one or more processors can determine a plurality of arterial flow velocities (e.g., associated with a plurality of pairs of points) for each segment.

When multiple arterial flow velocities (or rates) are determined for a segment of a coronary artery structure, the one or more processors can use statistical methods, such mean, median, minimum, maximum, or a histogram to determine an arterial flow velocity (or rate) of the segment based on the multiple determined velocities (or rates).

What is claimed is:

1. A method of generating arterial flow signals based on computed tomography projections, the method comprising:
    obtaining a three-dimensional (3D) image of an anatomical region including a coronary artery structure;
    constructing a 3D centerline of the coronary artery structure by removing voxels of the coronary artery structure in the 3D image to reduce a thickness of the coronary artery structure, constructing the 3D centerline including determining, at voxels along the 3D centerline, one or more corresponding diameters of the coronary artery structure;
    projecting the 3D centerline on each CT projection image of a set of CT projection images to identify one or more two-dimensional (2D) centerlines of the coronary artery structure on the CT projection image;
    determining, for each pixel of the one or more 2D centerlines of the coronary artery structure, a corresponding background intensity value using a diameter of the coronary artery structure associated with the pixel of the one or more 2D centerlines of the coronary artery structure; and
    subtracting, from each pixel of the one or more 2D centerlines of the coronary artery structure, the corresponding background intensity value to generate arterial pixel intensity values along the one or more 2D centerlines of the coronary artery structure with mitigated background interference.

2. The method of claim 1, wherein constructing the 3D centerline of the coronary artery structure includes at least one of:
    using a thinning algorithm to reduce the thickness of the coronary artery structure; or
    using a surface-based approach to reduce the thickness of the coronary artery structure.

3. The method of claim 1 comprising:
    obtaining two or more 3D images of the anatomical region, each 3D image associated with a respective state of a plurality of states of the coronary artery structure;
    constructing, from each of the two or more 3D images of the anatomical region, a respective 3D centerline of the coronary artery structure;
    projecting each 3D centerline of the two or more 3D centerlines on a corresponding set of CT projection images.

4. The method of claim 1, wherein determining, for each pixel of the one or more 2D centerlines of the coronary artery structure, a corresponding background intensity value includes:
    determining a background pixel that is located, within a CT projection image including the pixel of the 2D centerlines of the coronary artery structure, away from the one or more 2D centerlines of the coronary artery structure by at least half of a diameter of the coronary artery structure associated with the pixel of the one or more 2D centerlines of the coronary artery structure; and
    determining the corresponding background intensity value as an intensity value of the background pixel.

5. The method of claim 1, wherein determining, for each pixel of the one or more 2D centerlines of the coronary artery structure, a corresponding background intensity value includes:
    determining a plurality of background pixels that are each located, within a CT projection image including the pixel of the one or more 2D centerlines of the coronary artery structure, away from the 2D centerlines of the coronary artery structure by at least half of a diameter of the coronary artery structure associated with the pixel of the one or more 2D centerlines of the coronary artery structure; and
    determining the corresponding background intensity value using intensity values of the plurality of background pixels, the corresponding background attenuation value determined as:
    an average of intensity values of the plurality of background pixels;
    a maximum value from intensity values of the plurality of background pixels; or
    a minimum value from intensity values of the plurality of background pixels.

6. The method of claim 1 comprising:
    determining, for each first pixel of the one or more 2D centerlines in a first CT projection image, a corresponding second pixel of the one or more 2D centerlines in a second CT projection image, the first and second CT projection images acquired simultaneously at two distinct projection angles, and the first and second pixels of the 2D centerlines corresponding to a first voxel of the 3D centerline;
    determining a plurality of background pixels that are each located, within the second CT projection image, away from the second pixel by at least half of a diameter of the coronary artery structure associated with the first voxel of the 3D centerline; and determining the corresponding background intensity value using intensity values of the plurality of background pixels.

7. The method of claim 6, further comprising acquiring the set of CT projection images using two x-ray source-detector pairs oriented at an angle relative to each other, the two x-ray source-detector pairs simultaneously acquiring, at each acquisition time instance of a plurality of acquisition time instances, a corresponding pair of CT projection images.

8. A method of estimating arterial flow velocity in coronary arteries based on computed tomography (CT) projections, the method comprising:

obtaining a sequence of computed tomography (CT) projection images of an anatomical region including a coronary artery structure, the sequence of the CT projection images acquired by a CT scanner at a plurality of acquisition time instances;

generating, for a first point along a segment of the coronary artery structure, a corresponding first time attenuation sequence representing intensity values of the first point across the sequence of the CT projection images;

generating, for a second point along the segment of the coronary artery structure and different than the first point, a corresponding second time attenuation sequence representing intensity values of the second point across the sequence of the CT projection images;

determining, using the first time attenuation sequence and a time window, a first average transit time value representing an average time duration for arterial flow particles to reach the first point along the segment of the coronary artery structure;

determining, using the second time attenuation sequence and the time window, a second average time value representing an average time duration for arterial flow particles to reach the second point along the segment of the coronary artery structure; and determining an arterial flow velocity value between the first and second points along the segment of the coronary artery structure as a distance between the first and second points along the segment of the coronary artery structure divided by a difference between the first and second average transit time values.

9. The method of claim 8, wherein a time average value $T_i$, associated with a point $p_i$ along the segment of the coronary artery structure having an index i, for at least one of the first and second time average values, is determined as $$T(p_i) = \frac{\sum_{t_k \in W} t_k \cdot I_i(t_k)}{\sum_{t_k \in W} I_i(t_k)}$$

where W represents the time window, $t_k$ represents an acquisition time instance, and $I_i(t_k)$ represent an intensity value of the point $p_i$ in the CT projection image acquired at acquisition time instance $t_k$.

10. The method of claim 8, comprising:

determining, for each point along a centerline of the segment of the coronary artery structure, a corresponding time attenuation sequence representing intensity values of the point along the centerline across the sequence of the CT projection images;

determining, for each point along the centerline of the segment of the coronary artery structure using the corresponding time attenuation sequence associated with the point along the centerline, a corresponding average transit time value representing an average time duration for arterial flow particles to reach the point along the centerline of the segment of the coronary artery structure; and computing a plurality of arterial flow velocity values, each arterial flow velocity value representing arterial flow velocity between a corresponding pair of points along the centerline of the segment of the coronary artery structure and computed as a distance between the pair of points along the centerline divided by a difference between a pair of average transit time values associated with the pair of points along the centerline of the segment of the coronary artery structure.

11. The method of claim 8, wherein the sequence of CT projection images is a first sequence of CT projection images, the arterial flow velocity value is a first arterial flow velocity value, and the method further comprising:

obtaining a second sequence of CT projection images of the anatomical region, the second sequence of CT projection images acquired by the CT scanner at a second plurality of acquisition time instances;

generating, for the first point along the segment of the coronary artery structure, a corresponding third time attenuation sequence representing intensity values of the first point across the second sequence of the CT projection images;

generating, for the second point along the segment of the coronary artery structure, a corresponding fourth time attenuation sequence representing intensity values of the second point across the second sequence of the CT projection images;

determining, using the third time attenuation sequence and the time window, a third average transit time value representing another average time duration for arterial flow particles to reach the first point along the segment of the coronary artery structure;

determining, using the second time attenuation sequence and the time window, a fourth average time value representing another average time duration for arterial flow particles to reach the second point along the segment of the coronary artery structure; and computing a second arterial flow velocity value representing arterial flow velocity between the first and second points along the segment of the coronary artery structure as a distance between the first and second points along the segment of the coronary artery structure divided by a difference between the third and fourth average transit time values.

12. The method of claim 11, further comprising:

injecting a vasodilator drug into a patient associated with the anatomical region to cause dilation of blood vessels between acquisition of the first sequence of CT projection images and acquisition of the second sequence of CT projection images by the CT scanner; and comparing the first and second arterial flow velocity values to determine abnormalities, if any, of the coronary artery structure.

13. The method of claim 8, wherein the first and second points are located along a centerline of the segment of the coronary artery structure, and the method further comprises identifying the centerline of the segment of the coronary artery structure in each CT projection image of the sequence of CT projection images.

14. The method of claim 8 further comprising:
subtracting, prior to generating the first time attenuation curve, background intensity values from intensity values of the first point across the sequence of CT projection images to adjust the intensity values of the first point;
subtracting, prior to generating the second time attenuation curve, background intensity values from intensity values of the second point across the sequence of CT projection images to adjust the intensity values of the second point; and
generating the first and second time attenuation curves using the adjusted intensity values of the first point and the adjusted intensity values of the second point, respectively.

15. A method of estimating arterial flow velocity in coronary arteries based on computed tomography projections, the method comprising:
obtaining a sequence of computed tomography (CT) projection images of an anatomical region including a coronary artery structure, the sequence of CT projection images acquired by a CT scanner at a plurality of acquisition time instances;
generating, for a first point along a segment of the coronary artery structure, a corresponding first time attenuation sequence representing the intensity of the first point across the sequence of the CT projection images;
generating, for a second point along the segment of the coronary artery structure, a corresponding second time attenuation sequence representing the intensity of the second point across the sequence of the CT projection images;
determining, using the first time attenuation sequence associated with the first point along the segment of the coronary artery structure, a first cumulative sum of intensities of the first point across a first time interval;
determining, for the second point along the segment of the coronary artery structure using the second time attenuation sequence, a second time interval across which a second cumulative sum of intensities of the second point matches the first cumulative sum; and
determining an arterial flow velocity value representing arterial flow velocity between the first and the second points along the segment of the coronary artery structure as a distance between the first and the second points along the segment of the coronary artery structure divided by a difference between the first and second time intervals.

16. The method of claim 15, wherein the first cumulative sum of intensities $CS_1$ ($T_1$) of the first point across a first time interval [0, $T_1$] is determined as $CS_1$ ($T_1$)=$\Sigma_{t_k \in [0, T_1]} I_1(t_k)$, where $t_k$ represents an acquisition time instance, and $I_1(t_k)$ represents an intensity value of the first point in the CT projection image acquired at the acquisition time instance $t_k$.

17. The method of claim 15 comprising:
determining, for each point along a centerline of the segment of the coronary artery structure, a corresponding time attenuation sequence representing intensity values of the point along the centerline across the sequence of the CT projection images;
determining, for each point along the centerline of the segment of the coronary artery structure using the corresponding time attenuation sequence associated with the point along the centerline, a corresponding cumulative sum function representing sums of intensities of the point along the centerline of the segment of the coronary artery structure across a plurality of time intervals;
determining a plurality of pairs of points along the centerline of the segment of the coronary artery structure; and
computing, for each pair of points of the plurality of pairs of points, a corresponding arterial flow velocity value using a distance between the pair of points and a pair of cumulative sum functions associated with the pair of pints.

18. The method of claim 15, wherein the sequence of CT projection images is a first sequence of CT projection images, the arterial flow velocity value is a first arterial flow velocity value, and the method further comprising:
obtaining a second sequence of CT projection images of the anatomical region, the second sequence of CT projection images acquired by the CT scanner at a second plurality of acquisition time instances;
generating, for the first point along the segment of the coronary artery structure, a corresponding third time attenuation sequence representing intensity values of the first point across the second sequence of the CT projection images;
generating, for the second point along the segment of the coronary artery structure, a corresponding fourth time attenuation sequence representing intensity values of the second point across the second sequence of the CT projection images;
determining, using the third time attenuation sequence associated with the first point along the segment of the coronary artery structure, a third cumulative sum of intensities of the first point across a third time interval;
determining, for the second point along the segment of the coronary artery structure using the fourth time attenuation sequence, a fourth time interval across which a fourth cumulative sum of intensities of the second point matches the third cumulative sum; and
determining a second arterial flow velocity value representing arterial flow velocity between the first and second points along the segment of the coronary artery structure as a distance between the first and second points along the segment of the coronary artery structure divided by a difference between the third and fourth time intervals.

19. The method of claim 18 further comprising:
injecting a vasodilator drug into a patient associated with the anatomical region to cause dilation of blood vessels between acquisition of the first sequence of CT projection images and acquisition of the second sequence of CT projection images by the CT scanner; and
comparing the first and second arterial flow velocity values to determine abnormalities, if any, of the coronary artery structure.

20. The method of claim 15 further comprising:
subtracting, prior to generating the first time attenuation curve, background intensity values from intensity values of the first point across the sequence of CT projection images to adjust the intensity values of the first point;
subtracting, prior to generating the second time attenuation curve, background intensity values from intensity values of the second point across the sequence of CT projection images to adjust the intensity values of the second point; and generating the first and second time attenuation curves using the adjusted intensity values of the first point and the adjusted intensity values of the second point, respectively.

* * * * *